(12) United States Patent
Andres et al.

(10) Patent No.: US 11,971,407 B2
(45) Date of Patent: Apr. 30, 2024

(54) DETECTION OF ANTI-P53 ANTIBODIES

(71) Applicant: Roche Diagnostics Operations, Inc., Indianapolis, IN (US)

(72) Inventors: Herbert Andres, Penzberg (DE); Johann Karl, Peissenberg (DE); Ursula Kunert, Munich (DE); David Morgenstern, Indianapolis, IN (US); Nina Meissler, Huglfing (DE); Marion Niessner, Penzberg (DE); Magdalena Swiatek-de Lange, Penzberg (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 17/730,403

(22) Filed: Apr. 27, 2022

(65) Prior Publication Data

US 2022/0252592 A1 Aug. 11, 2022

Related U.S. Application Data

(63) Continuation of application No. 16/111,347, filed on Aug. 24, 2018, now abandoned, which is a continuation of application No. PCT/EP2017/055190, filed on Mar. 6, 2017.

(30) Foreign Application Priority Data

Mar. 7, 2016 (EP) .................................... 16158911

(51) Int. Cl.
*G01N 33/53* (2006.01)
*C07K 16/46* (2006.01)
*G01N 33/564* (2006.01)
*G01N 33/574* (2006.01)

(52) U.S. Cl.
CPC ........... *G01N 33/564* (2013.01); *C07K 16/46* (2013.01); *G01N 33/574* (2013.01); *G01N 33/5748* (2013.01); *G01N 33/57496* (2013.01)

(58) Field of Classification Search
None
See application file for complete search history.

(56) References Cited

U.S. PATENT DOCUMENTS

| | | | |
|---|---|---|---|
| 4,275,149 | A | 6/1981 | Litman et al. |
| 4,318,980 | A | 3/1982 | Boguslaski et al. |
| 4,737,456 | A | 4/1988 | Weng et al. |
| 5,221,605 | A | 6/1993 | Bard et al. |
| 5,591,581 | A | 1/1997 | Massey et al. |
| 5,597,910 | A | 1/1997 | Gudibande et al. |
| 5,679,519 | A | 10/1997 | Oprandy |
| 9,261,510 | B2 | 2/2016 | Schotz et al. |
| 2002/0058280 | A1 | 5/2002 | Singh et al. |
| 2010/0240068 | A1 | 9/2010 | Karl et al. |
| 2015/0232560 | A1 | 8/2015 | Heindl et al. |

FOREIGN PATENT DOCUMENTS

| | | |
|---|---|---|
| EP | 1982993 B1 | 7/2011 |
| EP | 2706115 A1 | 3/2014 |
| EP | 2827146 A1 | 1/2015 |
| JP | 2008263983 A | 11/2008 |
| JP | 2015028479 A | 2/2015 |
| WO | 1987006706 A1 | 11/1987 |
| WO | 1990005296 A1 | 5/1990 |
| WO | 1990005301 A1 | 5/1990 |
| WO | 1992014139 A1 | 8/1992 |
| WO | 1994010306 A1 | 5/1994 |
| WO | 1995008644 A1 | 3/1995 |
| WO | 1995025882 A1 | 9/1995 |
| WO | 1996006946 A1 | 3/1996 |
| WO | 1996018409 A1 | 6/1996 |
| WO | 1996024690 A1 | 8/1996 |
| WO | 1996033411 A1 | 10/1996 |
| WO | 1996039534 A1 | 12/1996 |
| WO | 1996040978 A1 | 12/1996 |
| WO | 1996041175 A1 | 12/1996 |
| WO | 1997033176 A1 | 9/1997 |
| WO | 1998012539 A1 | 3/1998 |
| WO | 2009074276 A2 | 6/2009 |
| WO | 2010150254 A2 | 12/2010 |
| WO | 2012028697 A1 | 3/2012 |
| WO | 2015128394 A2 | 9/2015 |

OTHER PUBLICATIONS

Chinese Master Thesis (? Sue, this is in the email of Apr. 8, 2022). Pan Hui, "Evaluation of the diagnostic value of P53 antibody and small nuclear ribonuelioprotein U1-A antibody to non-small cell lung cancer (NSCLC) by using ROC curve", 2012.
Inosaka, Yoshitaka, Relation between FGF23 value of serum in storage period and CVD event during, before, and after dialysis, Journal of Japanese Society for Dialysis Therapy, 2012, p. 350, vol. 45, Supplement 1, SY-5-1.
Kato, Hideki, A chronic kidney disease and phosphate metabolism, Annual Review of Kidney, 2012, pp. 171-177.
Suzuki, Masashi, What is FGF23 Responsible for?, Quarterly Journal of Dialysis, 2010, pp. 25-26, vol. 20, No. 3.
Benchimol, Sam et al., Radioimmunoassay of the cellular protein p53 in mouse and human cell lines, The EMBO Journal, 1982, pp. 1055-1062, vol. 1, No. 9.
Briggs, Mark S. J_ et al., Synthesis of functionalised fluorescent dyes and their coupling to amines and amino acids, Journal of the American Chemical Society, Perkin Trans. 1, 1997, pp. 1051-1058.

(Continued)

*Primary Examiner* — Gary Counts
(74) *Attorney, Agent, or Firm* — Stinson LLP

(57) ABSTRACT

An in vitro method is disclosed for detecting an antibody to p53 (anti-p53 antibody) in a sample, the method comprising: incubating a sample to be analyzed with a p53 capture antigen and a p53 detection antigen, whereby a complex comprising the p53 capture antigen, the anti-p53 antibody and the p53 detection antigen is formed, separating the complex formed from unbound detection antigen and measuring the complex obtained via the detection antigen comprised therein, thereby detecting the anti-p53 antibody comprised in the sample.

18 Claims, 2 Drawing Sheets

Specification includes a Sequence Listing.

(56) References Cited

OTHER PUBLICATIONS

Greenblatt, M. S. et al., Mutations in the p53 Tumor Suppressor Gene: Clues to Cancer Etiology and Molecular Pathogenesis, Cancer Research, 1994, pp. 4855-4878, vol. 54.

Knight, Andrew W. and Greenway, Gillian M., Occurrence, Mechanisms and Analytical Applications of Electrogenerated Chemiluminescence a Review, Analyst, 1994, pp. 879-890, vol. 119.

Levine, Arnold J., p53, the Cellular Gatekeeper for Growth and Division, Cell, 1997, pp. 323-331, vol. 88.

O'Sullivan, M. J_ and Marks, V., Methods for the Preparation of Enzyme-Antibody Conjugates for Use in Enzyme Immunoassay, Methods in Enzymology, 1981, pp. 147-166, vol. 73.

Soussi, Thierry, p53 Antibodies in the Sera of Patients with Various Types of Cancer: A Review, Cancer Research, JOOO, pp. 1771-1788, vol. 60, 2000.

Crawford, L. V. et al., Detection of Antibodies Against the Cellular Protein p53 in Sera from Patients with Breast cancer, International Journal of Cancer, 1982, pp. 403-408, vol. 30.

International Search Report dated Apr. 25, 2017, in Application No. PCT/EP2017/055190, 3 pages.

Portefaix, Jean-Michel et al., Detection of anti-p53 antibodies by ELISA using p53 synthetic or phage-displayed peptides, Journal of Immunological Methods, 2002, pp. 65-75, vol. 259.

Meng et al., Development and Application of a Double-Antigen Sandwich Enzyme-Linked Immunosorbent Assay for Detection of Antibodies to Porcine Circovirus 2, Clinical and Vaccine Immunology, vol. 19, No. 9, Sep. 2012, pp. 1480-1486.

Portefaix et al., Detection of anti-p53 antibodies by ELISA using p53 synthetic orphage-displayed peptides, Journal of Immunological Methods, Vo. 259, 2002, pp. 65-75.

Ryder et al., J Clin Pathol 1996, vol. 49, pp. 295-299.

Crawford et al., Int J Cancer, 1982, Oct. 15, vol. 30, No. 4, pp. 403-408.

Banks L., Matlashewski G. and Crawford L. Isolation of human-p53 specific monoclonal antibodies and their use in the studies of human p53 expression. Eur. J. Biochem., vol. 159, pp. 529-534, 1986.

Lubin et al., Cancer Res., vol. 53 (1993), pp. 5872-5876.

DETECTION OF ANTI-P53 ANTIBODIES

CROSS REFERENCE TO RELATED APPLICATIONS

This application is a continuation of U.S. patent application Ser. No. 16/111,347 (published as U.S. Publication No. 2018/0364230, now abandoned), filed Aug. 24, 2018, which is a continuation of International Application No. PCT/EP2017/055190 filed Mar. 6, 2017, which claims priority to European Application No. 16158911.4 filed Mar. 7, 2016, the disclosures of which are hereby incorporated by reference in their entirety.

INCORPORATION OF SEQUENCE LISTING

A paper copy of the Sequence Listing and a computer readable form of the Sequence Listing containing the file named "P33437-US1 Sequence Listing ST25", which is 6,891 bytes in size (as measured in MICROSOFT WINDOWS® EXPLORER), are provided herein and are herein incorporated by reference. This Sequence Listing consists of SEQ ID NOs: 1-4.

BACKGROUND OF THE INVENTION

The present disclosure relates to a method for the detection of antibodies against p53 (anti-p53 antibodies). The method disclosed, enables the detection of anti-p53 antibodies with higher specificity as compared to state of the art methods. The method according to the present disclosure requires a p53 capture antigen and a p53 detection antigen. The method comprises incubating a p53 capture antigen and a p53 detection antigen with a sample known or suspected to comprise an anti-p53 antibody, whereby a complex comprising the p53 capture antigen the anti-p53 antibody and the p53 detection antigen is formed, separating the complex formed from unbound detection antigen, measuring the complex obtained via the detection antigen comprised therein and thereby detecting the anti-p53 antibody comprised in the sample.

Anti-p53 antibodies (anti-p53 Abs) were discovered more than 30 years ago during the course of tumor-associated antigen screening, Crawford L. V. et al., Int. J. Cancer, 30: 403-408, 1982. However, this study as well as a few similar ones, performed in the early 1980s, were virtually ignored for more than 10 years because of a lack of interest in p53 during that period.

In the early 1990s, it was discovered that the p53 gene is the most common target for molecular alteration in almost every type of human cancer. This provoked considerable interest in the study of the p53 protein and its function in normal and transformed cells. It also led to the rediscovery of the humoral response, which had been found earlier already in cancer patients.

The tumor suppressor p53 is a phosphoprotein barely detectable in the nucleus of normal cells (Benchimol, S. et al., EMBO J. 1 (1982) 1055-1062). On cellular stress, particularly that induced by DNA damage, p53 can arrest cell cycle progression, thus allowing the DNA to be repaired or it can lead to apoptosis. In cancer cells that bear a mutant p53, this protein is no longer able to control cell proliferation, which results in inefficient DNA repair (Levine, A. Cell 88 (1997) 323-331). The most common changes of p53 in human cancer are point missense mutations, which are found in cancers of the colon, stomach, breast, lung, brain and esophagus (Greenblatt, M. et al., Cancer Res. 54 (1994) 4855-4878). It is estimated that p53 mutations is the most frequent genetic event in human cancers and accounts for more than 50% of cases. There is a very strong correlation between the frequency of p53 antibodies and the frequency of p53 mutations arguing that p53 mutations are involved in the appearance of these antibodies (Soussi, T. Cancer Res. 60 (2000) 1777-1788). Anti-p53 antibodies are found in human cancer patients with a specificity of about 96%, but the sensitivity of such detection is only about 30%.

The association of p53 mutations with anti-p53 antibodies suggests that the anti-p53 humoral immune response is due to a self-immunization process linked to the strong immunogenicity of the p53 protein.

The role of p53 mutations in carcinogenesis has been extensively studied and anti-p53 antibodies have been found to be associated to numerous cancer types such as Colorectal Cancer (CRC), Oesophageal Cancer and Breast Cancer among others. These 3 cancer types represent a considerable healthcare burden.

With an incidence of 746,000 cases/year in men, CRC is the third most common cancer in men worldwide and represents 10.0% of the total cancers among male patients. CRC is also the second most common in women across the world with 614,000 new cases each year, representing 9.2% of cancers affecting female patients. Oesophageal cancer is the sixth most common cause of death from cancer and has an estimated incidence of 456,000 new cases among men and women representing 3.2% of the total new cancers each year. Breast Cancer is by far the most frequent cancer among women with an estimated 1.67 million new cancer cases diagnosed worldwide in 2012 representing 25% of all cancers in female patients. Overall, Breast cancer is the second most common cancer in the world. As obvious from the high incidence of cancer types associated with anti-p53 (auto-) antibodies, there is a need for a sensitive and reliable diagnostic method for detection of anti-p53 (auto-)antibodies.

As summarized by Soussi, T. (Cancer Research 60 (2000) 1777-1788) many papers on anti-p53 have been published. The detection methods used vary significantly with ELISA-methods, immuno precipitation methods and Western Blotting being the most prominent ones. It may well be that the use of many different methods for detection of anti-p53 antibodies has lead to some discrepant results and to some uncertainty regarding the diagnostic utility of anti-p53 antibodies.

The availability of the first commercial assays for measurement of anti-p53 antibodies has been of great value in improving the comparability of data/papers on anti-p53 antibodies. One of the most frequently used assay for measurement of anti-p53 antibodies is "MESACUP Anti-p53 TEST" distributed by MEDICAL & BIOLOGICAL LABORATORIES CO., LTD., KDX Nagoya, Japan. This Enzyme immunoassay for the detection of anti-p53 IgG in human serum is laborious and e.g. requires the parallel measurement of both specific (including non-specific) and non-specific binding, respectively. The fraction of specific binding has then to be calculated by subtraction of the value determined for non-specific binding from the sum of specific and non-specific binding.

Antibodies of the IgM class of antibodies in general are more sticky and lead to further complications, e.g. further cross-reactivity and non-specific binding. For this reason anti-p53 detection methods in most cases rely on anti-human IgG detection reagents, i.e. the detection of only the human (auto-) antibodies of the immunoglobulin G class and not those of the immunoglobulin M class. As further evidenced by the way the Mesacup assay has to be performed, non-specific binding most likely is a key problem for any method used in the detection of anti-p53 antibodies.

As obvious from the high incidence of cancer types associated with anti-p53 (auto-) antibodies, and as further evident from the drawbacks with state of the art methods used to detect those antibodies there is a tremendous need for a sensitive and reliable immuno assay method for detection of anti-p53 (auto-)antibodies.

It surprisingly has been found that the method for detecting anti-p53 (auto-) antibodies as disclosed herein below is rapid, reliable, specific, sensitive and has the potential to set a new standard in the detection of anti-p53 (auto-) antibodies.

SUMMARY OF THE INVENTION

Herein is reported an in vitro method for detecting an antibody to p53 (anti-p53 antibody) in a sample, the method comprising: a) incubating a sample to be analyzed with a p53 capture antigen and a p53 detection antigen, whereby a complex comprising the p53 capture antigen, the anti-p53 antibody and the p53 detection antigen is formed, b) separating the complex formed in (a) from unbound detection antigen, c) measuring the complex obtained in step (b) via the detection antigen comprised therein, thereby detecting the anti-p53 antibody comprised in the sample. Further and more detailed embodiments relate, e.g., to specific partial sequences of p53 for use in a method according to the present disclosure.

Figure 1:
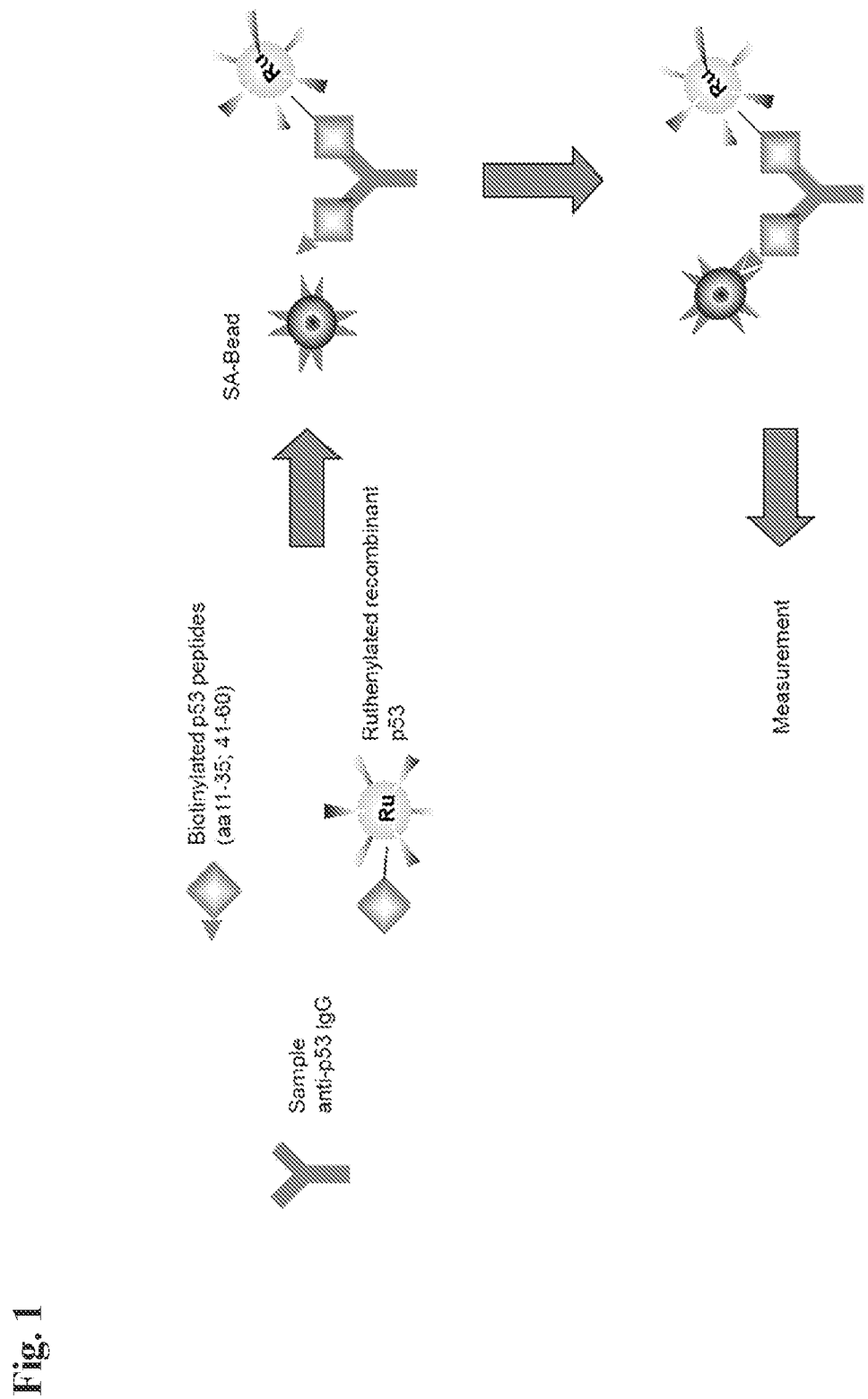
FIG. 1 Assay principle of Elecsys anti-p53 assay

The double antigen sandwich assay (DAGS) format is schematically depicted.=>detection of anti-p53 auto-antibodies present in the sample is accomplished via biotinylated capture antigen (binding to streptavidin coated to paramagnetic beads) and ruthenylated p53 detection antigen.

FIG. 2 ROC-Blots

For both assays analyzed, the receiver-operator-curves (ROCs) are given. The ROC for the MesaCup assay is depicted as an interrupted line, whereas the ROC for the assays disclosed in the present application is given as continuous/full line.

DETAILED DESCRIPTION OF THE INVENTION

The present disclosure relates to an in vitro method for detecting an antibody to p53 (anti-p53 antibody) in a sample, the method comprising: a) incubating a sample to be analyzed with a p53 capture antigen and a p53 detection antigen, whereby a complex comprising the p53 capture antigen, the anti-p53 antibody and the p53 detection antigen is formed, b) separating the complex formed in (a) from unbound detection antigen, c) measuring the complex obtained in step (b) via the detection antigen comprised therein, thereby detecting the anti-p53 antibody comprised in the sample.

In the following the terms "anti-p53 (auto-) antibody", "anti-p53 antibody" or "p53 antibody" are used interchangeably. An anti-p53 antibody is an antibody that binds to the p53 polypeptide of SEQ ID NO: 3 or to a partial sequence thereof.

As mentioned above the method according to the present invention requires the use of both, a p53 capture antigen and of a p53 detection antigen, respectively. An antibody to p53 present in a sample to be investigated binds to both these antigens, thereby forming a complex comprising the p53 capture antigen, the anti-p53 antibody and the p53 detection antigen.

The term "capture antigen" is familiar to a person skilled in the art.

In order to perform a double antigen sandwich immuno assay it is required that one provides an epitope at least twice, at least once on the capture antigen to mediate binding to a solid phase, and at least once on the detection antigen to allow for detection of the sandwich complex (antigen-antibody-antigen) formed.

In one embodiment the p53 capture antigen is capable of binding to a solid phase.

Materials for manufacturing a solid phase (solid support) are well-known in the art. and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, wells and walls of reaction vessels, plastic tubes etc.

In one embodiment the solid phase is represented by the wells and walls of a microtitre plate.

In one embodiment the solid phase is in the form of particles. The particle may be a microparticle which is or which comprises magnetic or ferromagnetic metals, alloys or compositions. In further embodiments, the solid phase material may have specific properties and e.g. be hydrophobic, or hydrophilic. In one embodiment of the present invention, the microparticles are paramagnetic microparticles and the separation of such particles in the measurement method according to the present disclosure is facilitated by magnetic forces. Magnetic forces are applied to pull the paramagnetic or magnetic particles out of the solution/suspension and to retain them as desired while liquid of the solution/suspension can be removed and the particles can e.g. be washed.

As indicated above, in one embodiment the p53 capture antigen is capable of binding to a solid phase. In order for the capture antigen to be capable of binding to a solid phase it is preferred to employ a specific binding pair. One partner of such binding pair is bound to the capture antigen and the other partner of such binding pair is bound to the solid phase.

A "binding pair" as used herein consists of two partners binding to each other with high affinity, i.e. with one nanomolar affinity or better. Embodiments for binding pairs are for example the binding pairs consisting of receptor and ligand, antigen and antibody, hapten and anti-hapten antibody, and binding pairs based on naturally occurring high affinity binding pairs.

One example of a receptor-ligand binding pair is a pair consisting of a steroid hormone receptor and the corresponding steroid hormone.

One further type of a binding pair which is suitable for the method according to the present invention is a hapten and anti-hapten antibody binding pair. A hapten is an organic molecule with a molecular weight of 100 to 2000 Dalton, preferably of 150 to 1000 Dalton. Such small molecule which if used as such is non-immunogenic but can be rendered immunogenic by coupling it to a carrier molecule and anti-hapten antibodies can be generated according to standard procedures. The hapten may be selected from the group comprising sterols, bile acids, sexual hormones, corticoids, cardenolides, cardenolide-glycosides, bufadienolides, steroid-sapogenines and steroid alkaloids, cardenolides and cardenolide-glycosides. Representatives of these substance classes are digoxigenin, digitoxigenin, gitoxigenin, strophanthidin, digoxin, digitoxin, ditoxin, strophanthin. Another suitable hapten is for example fluorescein.

Examples of binding pairs based on naturally occurring high affinity binding pairs are biotin or biotin analogues such as aminobiotin, iminobiotin or desthiobiotin and avidin or streptavidin as well as the FimG and DsF binding pair. The biotin-(strept)avidin binding pair is well-known in the art. The basic principles of the FimG-DsF binding pair are e.g. described in WO2012/028697.

In one embodiment the p53 capture antigen is covalently bound to a first partner of a binding pair and the second partner of said binding pair is bound to the solid phase.

In one embodiment the first partner of the binding pair is selected from hapten, biotin or a biotin analogue such as aminobiotin, iminobiotin or desthiobiotin, DsF and the ligand for a receptor and the second partner of said binding pair is selected from anti-hapten antibody, avidin or streptavidin, FimG and a ligand-receptor.

In one embodiment first partner of the binding pair is selected from hapten, biotin or a biotin analogue such as aminobiotin, iminobiotin or desthiobiotin and DsF, and the second partner of said binding pair is selected from anti-hapten antibody, avidin or streptavidin and FimG.

In one embodiment first partner of the binding pair is selected from biotin or a biotin analogue, such as aminobiotin, iminobiotin or desthiobiotin, and DsF, and the second partner of said binding pair is selected from, avidin or streptavidin and FimG.

In one embodiment first partner of the binding pair is biotin or a biotin analogue such as aminobiotin, iminobiotin or desthiobiotin and the second partner of said binding pair is selected from avidin or streptavidin.

In one embodiment first partner of the binding pair is biotin and the second partner of said binding pair is streptavidin.

In one embodiment the method according to the present invention is practiced with a p53 capture antigen that is biotinylated and a solid phase that is coated with avidin or streptavidin.

It is, however, also possible to directly bind the capture antigen to a solid phase. In one embodiment the method according to the present invention is practiced with a p53 capture antigen that is bound to the solid phase.

Antibodies are at least bi-valent, i.e. having the potential to bind with one 'arm' to the capture antigen and with the other arm (or any of the other arms for multivalent antibodies) to the detection antigen.

An antibody to p53 present in a sample to be investigated binds to both these antigens, thereby forming a complex comprising the capture antigen, the anti-p53 antibody and the detection antigen.

The skilled artisan is familiar with the term "detection antigen".

The term detection antigen implies that this antigen can be detected. Such detection can be accomplished by various types of labels which are either directly or indirectly detectable.

In one embodiment the method according to the present disclosure is a method wherein the p53 detection antigen comprises a directly detectable label.

The term detectably labeled encompasses labels that can be directly or indirectly detected.

Directly detectable labels either provide a detectable signal or they interact with a second label to modify the detectable signal provided by the first or second label, e.g. to give FRET (fluorescence resonance energy transfer). Labels such as fluorescent dyes and luminescent (including chemiluminescent and electrochemiluminescent) dyes (Briggs et al "Synthesis of Functionalised Fluorescent Dyes and Their Coupling to Amines and Amino Acids," J. Chem. Soc., Perkin-Trans. 1 (1997) 1051-1058) provide a detectable signal and are generally applicable for labeling. In one embodiment detectably labeled refers to a label providing or inducible to provide a detectable signal, i.e. to a luminescent label, to a fluorescent label, to a chemiluminescent label or to an electrochemiluminescent label, respectively.

In one embodiment according to the present disclosure the microparticle-based analyte-specific binding assay makes use of a chemiluminescent or an electrochemiluminescent label and a corresponding light detection system. The light produced by the label is measured and directly or indirectly indicates the presence or quantity of the analyte.

Electrochemiluminescent (ECL) assays provide a sensitive and precise measurement of the presence and concentration of an analyte of interest. Such techniques use labels or other reactants that can be induced to luminesce when electrochemically oxidized or reduced in an appropriate chemical environment. Such electrochemiluminescense is triggered by a voltage imposed on a working electrode at a particular time and in a particular manner. The light produced by the label is measured and indicates the presence or quantity of the analyte. For a fuller description of such ECL techniques, reference is made to U.S. Pat. Nos. 5,221,605, 5,591,581, 5,597,910, PCT published application WO90/05296, PCT published application WO92/14139, PCT published application WO90/05301, PCT published application WO96/24690, PCT published application US95/03190, PCT application US97/16942, PCT published application US96/06763, PCT published application WO95/08644, PCT published application WO96/06946, PCT published application WO96/33411, PCT published application WO87/06706, PCT published application WO96/39534, PCT published application WO96/41175, PCT published application WO96/40978, PCT/US97/03653 and U.S. patent application Ser. No. 08/437,348 (U.S. Pat. No. 5,679,519). Reference is also made to a 1994 review of the analytical applications of ECL by Knight, et al. (Analyst, 1994, 119: 879-890) and the references cited therein. In one embodiment the method according to the present description is practiced using an electrochemiluminescent label.

In one embodiment the directly detectable label (used to label the detection antigen in a method of the present disclosure) is selected from the group consisting of a luminescent label, a fluorescent label, a chemiluminescent label or an electrochemiluminescent label.

In one embodiment the directly detectable label is a chemiluminescent or an electrochemiluminescent label.

In one embodiment the double-antigen sandwich assay according to the present disclosure uses the full length p53 polypeptide of SEQ ID NO:3 both as the capture as well as the detection antigen.

A synthetic peptide, representing at least one important epitope of p53 of the p53 polypeptide is of high utility in a method according to the present disclosure. Without wanting to be bound to theory, it may well be that such synthetic peptide sequence comprises an epitope that is bound by a significant percentage of those antibodies in a sample that also bind to the full-length p53 polypeptide. At the same time it may well be that those stretches of the p53 polypeptide that are rarely or not at all bound by an anti-p53 antibody (as e.g. comprised in a bodily fluid sample) are those sequence stretches that significantly contribute to the non-specific binding of antibodies, especially of the sticky IgM-class antibodies.

In one embodiment the in vitro method for detection of anti-p53 antibodies according to the present invention is a double antigen sandwich immuno assay method wherein both the p53 capture antigen and the p53 detection antigen comprise a peptide of SEQ ID NO: 1.

In one embodiment the in vitro method for detection of anti-p53 antibodies according to the present invention is a double antigen sandwich immuno assay method wherein both the p53 capture antigen and the p53 detection antigen comprise a peptide of SEQ ID NO: 2.

In one embodiment the method for detection of anti-p53 antibodies according to the present invention is a double antigen sandwich immuno assay method wherein the peptides of SEQ ID NO:1 and of SEQ ID NO:2 are each comprised in both the p53 capture antigen and the p53 detection antigen.

In one embodiment the peptides representing the relevant partial sequences of the p53 polypeptide used in a method for detection of anti-p53 antibodies according to the present invention are the peptides consisting of SEQ ID NO:1 and of SEQ ID NO:2, respectively.

In one embodiment the method for detection of anti-p53 antibodies according to the present invention is a double antigen sandwich immuno assay method wherein the p53 detection antigen is a single polypeptide comprising both the peptides of SEQ ID NO:1 and of SEQ ID NO:2 at least twice.

In one embodiment the method for detection of anti-p53 antibodies according to the present invention is a double antigen sandwich immuno assay method wherein the p53 detection antigen comprises a fusion polypeptide comprising at least one multimerization domain, at least one polypeptide of SEQ ID NO: 1 and at least one polypeptide of SEQ ID NO:2, wherein the multimerization domain is a prokaryotic or eukaryotic chaperone selected from the group consisting of FkpA, Skp, SecB, Hsp25, MIP, GroEL, ClpB and ClpX.

In one embodiment the present disclosure relates to a fusion polypeptide comprising at least one multimerization domain, at least one polypeptide of SEQ ID NO:1 and at least one polypeptide of SEQ ID NO:2, wherein the multimerization domain is a prokaryotic or eukaryotic chaperone selected from the group consisting of FkpA, Skp, SecB, Hsp25, MIP, GroEL, ClpB and ClpX.

The multimerization domain is preferably located at the N- and/or C-terminus of the fusion polypeptide, more preferably at the N-terminus. The multimerization domain is a polypeptide sequence which supports multimerization of individual fusion polypeptide molecules, wherein a multimer is formed which is comprised of a plurality of monomeric subunits, which are associated by non-covalent interactions. The monomeric subunits of the complex are genetic fusion proteins, wherein the individual amino acid residues are linked by peptide bonds. The monomeric subunits of the multimer are preferably identical.

For example, the multimerization domain may be a dimerization domain, i.e. a domain which supports noncovalent association of two subunits, a trimerization domain, which supports non-covalent association of three subunits, a tetramerization domain or an even higher mukimerization domain. Preferably, the multimerization domain is a dimerization domain, a trimerization domain or a tetramerization domain.

Multimerization domains may be selected from prokaryotic or eukaryotic chaperones, preferably from ATPindependent chaperones. Specific examples of multimerization domains are the proteins FkpA, Skp and SecB from *E. coli* or orthologs thereof from other prokaryotic organisms. FkpA is an ATP-independent periplasmic dimerization chaperone from *E. coli*. Skp is an ATP-independent periplasmic trimerization chaperone from *E. coli*. SecB is an ATPindependent cytosolic tetramerization chaperone from *E. coli*. Further suitable multimerization domains are heat shock proteins from eukaryotic or prokaryotic organisms, e.g. Hsp25, an ATP-independent eukaryotic cytosolic/nuclear oligomeric chaperone. A further suitable multimerization domain is MIP (macrophage infectivity potentiator), an ATP-independent dimerization chaperone which is structurally related with FkpA. ATP-dependent chaperones like GroEL, an ATP-dependent cytosolic heptamerisation chaperone from *E. coli* or ClpB, an ATP-dependent hexamerization chaperone from *E. coli* or ClpX are also suitable. Further, the multimerization domains may be selected from fragments or variants of the above polypeptides, which retain their ability of multimer formation.

The individual polypeptide sequences of SEQ ID NO:1 and of SEQ ID NO:2, respectively, in the fusion polypeptide may be separated by spacer sequences. The spacer sequences are preferably sequences which are heterologous to the p53. For practical purposes, the spacer sequences are selected from sequences which barely if at all interfere with the use of the fusion polypeptide as an antigen for determining anti-p53 antibodies. This means that the spacer sequences are not immunologically reactive against the antibodies to be tested. E.g., the spacer sequences comprise glycine and/or serine residues. In one embodiment the spacer is a poly-glycine spacer. The length of the spacer sequence is preferably from 1-10 amino acids.

Further, a spacer sequence may be present between the multimerization domain and the polypeptide of SEQ ID NO:1 and/or the polypeptide of SEQ ID NO:2.

This spacer sequence may have a length of e.g. 1-100 amino acids. Preferably, this spacer sequence is as described above.

In one embodiment the method according to the present disclosure is practiced with a p53 detection antigen comprising an indirectly detectable label.

Indirectly detectably labeled refers, e.g. to a detection antigen comprising a hapten and to the detection of such haptenylated compound by an anti-hapten antibody carrying a directly detectable label or to the a detection antigen comprising an enzyme and to the detection of such enzyme by its corresponding enzymatic activity resulting in the conversion of an appropriate dye substrate. Various enzyme-substrate labels are available or disclosed (see e.g. U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), (3-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to polypeptides are described in O'Sullivan et al "Methods for the Preparation of Enzyme-Antibody Conjugates for use in Enzyme Immunoassay", in Methods in Enzym. (ed. by J. Langone & IT Van Vunakis), Academic Press, New York, 73 (1981) 147-166.

Examples of enzyme-substrate combinations (U.S. Pat. Nos. 4,275,149; 4,318,980) include, for example: Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB)); alkaline phosphatase (AP) with para-nitrophenyl phosphate as chromogenic substrate; and (3-D-galactosidase ((3-D-Gal) with a chromogenic substrate (e.g., p-nitro phenyl-(3-D-galactosidase) or fluorogenic substrate 4-methylumbelliferyl-(3-D-galactosidase.

As mentioned above and as demonstrated in the Examples section, anti.p53 antibodies are most frequently found in CRC. In one embodiment the present invention relates to an in vitro method for diagnosing CRC by detecting an antibody to p53 (anti-p53 antibody) in a sample, the method comprising: a) incubating a sample to be analyzed with a p53 capture antigen and a p53 detection antigen, whereby a complex comprising the p53 capture antigen the anti-p53 antibody and the p53 detection antigen is formed, b) separating the complex formed in (a) from unbound detection antigen, c) measuring the complex obtained in step (b) via the detection antigen comprised therein, and d) diagnosing CRC if anti-p53 antibody is measured in the sample.

Liquid samples can be used in a method for specific in vitro-detection of anti-p53 antibodies in a method according to the present disclosure. The sample may be known to comprise an anti-p53 antibody or it may be suspected of comprising an anti-p53 antibody. In one embodiment the sample for in vitro diagnosis used in a method according to the present disclosure is a body fluid selected from whole blood, blood serum, blood plasma, liquor, urine or saliva. In one embodiment the sample suspected of comprising or comprising an anti-p53 antibody is serum, plasma or liquor. In one embodiment the sample suspected of comprising or comprising an anti-p53 antibody is serum or plasma.

The following examples and figures are provided to aid the understanding of the present invention, the true scope of which is set forth in the appended claims. It is understood that modifications can be made in the procedures set forth without departing from the spirit of the invention.

Example 1

Capture and Detection Antigen Used for Detection of Anti-p53 Auto-Antibodies

Various types of double antigen sandwich assay (DAGS) have been used.

It is possible to perform the DAGS assay for detection of anti-p53 auto-antibodies present in a sample as an enzyme-linked immuno sorbent assay (ELISA) in microtitre plates.

Synthetic peptides of SEQ ID NO:1 and SEQ ID NO:2, respectively proved to be advantageous. They could easily and reproduceably be synthesized and seemed to be appropriate due to the specific binding of anti-p53 antibodies thereto.

For higher through-put and higher reproduceability an anti-p53 assay was developed running on the automated electrochemiluminescense-based analyzers from Roche Diagnostics, Mannheim, Germany.

In one assays format two biotinylated peptides, one comprising the peptide of SEQ ID NO:1 and the other comprising the peptide of SEQ ID NO:2 are used as the capture antigen and the ruthenylated forms of both these peptides are used as the detection antigen.

1.1 The Biotinylated Peptides Used as Capture Antigen

As mentioned above both the sequence of SED ID NO:1 and SEQ ID NO:2, respectively, appear to comprise epitopes preferably bound by anti p53 (auto-) antibodies. Synthetic peptides comprising these sequences plus a linker consisting of three times the dipeptide glutamic acid (E)-ß-alanine (U) (=EU3) at their N-terminus were N-terminally coupled to activated biotin resulting in the two capture antigens jointly used in the Elecsys method described in more detail below. These biotinylated capture antigens were denominated as p53(11-35)[Bi(EU)3-11]amid and p53 (41-60)[Bi(EU)3-41] amid, respectively 1.2 The Ruthenylated Recombinant Fusion Protein Used as Detection Antigen It was found that it is possible to improve assay sensitivity by use of a multimeric detection antigen. The use of a multimeric antigen allows the binding of low affinity IgG-autoantibodies and/or also allows the binding of autoantibodies of the IgM type. To that end the p53 peptides of SEQ ID NO:1 (amino acids 11-35 of p53) and of SEQ ID NO:2 (amino acids 41-60 of p53) were expressed in *E. coli* as part of a recombinant polypeptide comprising Skp, SEQ ID NO:1 and SEQ ID NO:2 twice and an octa His-tag.

The sequence of the recombinant p53-construct (SEQ ID NO:4) was as follows:

MADKIAIVNMGSLFQQVAQKTGVSNTLENEFRGRASELQR

METDLQAKMKKLQSMKAGSDRTKLEKDVMAQRQTFAQKAQ

AFEQDRARRSNEERGKLVTRIQTAVKSVANSQDIDLVVDANAVAYNSSDV

KDITADVLKQVKGGGSGGGSGGGSGGGSGGGSEPPLSQET

FSDLWKLLPENNVLSPLPSQAMDDLMLSPDDIEQWFTEDP

GPGGGSGGGSGGGSGGGSGGGSEPPLSQETFSDLWKLLPENNVLSPL

PSQAMDDLMLSPDDIEQWFTEDPGPGGSHHHH HHHH

The underlined parts of the sequence represent SEQ ID NO:1 and SEQ ID NO:2, respectively. The sequence part given in cursory writing corresponds to the sequence derived from the chaperone Skp. The octa-His-tag is at the C-terminus of this recombinant polypeptide as used in the p53 detection antigen.

The recombinant polypeptide of SEQ ID NO:3 was produced according to procedures well known in the art and e.g. described in detail in EP 1 982 993 B1.

Ruthenylation was performed according to standard procedures. In a typical protocol for ruthenylation the lysine ε-amino groups of the fusion protein are modified at protein concentrations of about 10 mg/ml with N-hydroxy-succinimide activated ruthenium labels. The label:protein molar ratio can be varied from 2:1 to 7:1, depending on the respective fusion protein an requirements for density of labels. The reaction buffer usually is 150 mM potassium phosphate (pH 8.0), 50 mM potassium chloride, 1 mM EDTA. The coupling or labeling reaction usually is carried out at room temperature for 10 minutes and stopped by adding buffered L-lysine to a final concentration of 10 mM. To avoid hydrolytic inactivation of the activated labels, the respective stock solutions are e.g. prepared in dried DMSO (seccosolv quality, Merck, Germany). DMSO concentrations up to 20% in the reaction buffer are well tolerated by the fusion protein of SEQ ID NO:4 as disclosed herein. After the coupling reaction, unreacted free label and the organic solvent was removed by passing the crude protein conjugate over a gel filtration column (Superdex 200 HiLoad).

Due to the chaperon-part ("Skp") of the p53-construct, the protein spontaneously trimerizes during elution from the Ni-NTA column in the controlled refolding and purification process. The resulting trimer is very stable and remains its configuration during rhutenylation and further processing.

Example 2

Elecsys® Assay for Measurement of Anti-p53 Auto-Antibodies

The assay principle of the Elecsys® assay for detection of anti-p53 antibodies is depicted in FIG. 1.

In brief, the biotinylated capture antigen (the biotinylated peptides of Eample 1.1), the sample and the ruthenylated detection antigen (the labeled fusion protein of Example 1.2) are incubated to allow for formation of a complex of capture antigen—anti-p53 antibody—detection antigen. Signal detection in the Elecsys® immunoassay is based on electrochemoluminiscence. The biotin-conjugated capture antigen is immobilized on the surface of streptavidin-coated magnetic beads, whereas the detection antigen bears a complexed ruthenium cation as the luminescent moiety. In the presence of anti-p53 antibodies, the chromogenic ruthenium complex is bridged to the solid phase and emits light at 620 nm after excitation at a platinum electrode. The signal output is in arbitrary light units.

The following immunological reagents were used:

| Biotinylated capture antigen | Conc. | Ruthenylated detection antigen | Conc. |
|---|---|---|---|
| p53(11-35)[Bi(EU)3-11]amid | 20 ng/ml | rec.*E.coli* material | 300 ng/ml |
| p53(41-60)[Bi(EU)3-41]amid | 20 ng/ml | Skp-(p53 peptides)x2-BPRU | |

75 µl of the capture antigen comprising both peptides, each at the above given concentration, 75 lA of the detection antigen and 20 µl of sample were incubated for 9 min. Magnetic Elecsys® beads (30 µl were added and incubated for 9 min to adsorb the complex of capture antigen—ant-p53 antibody—detection antigen.

Signal measurement was performed on an Elecsys® e601 analyzer according to standard procedures.

The buffer used for the capture antigen comprises the following components:

| Buffer component | conc |
|---|---|
| Kaliumdihydrogenphosphat | 65 mM |
| Di-Kaliumhydrogenphosphat 1× H2O | 35 mM |
| NaCl | 150 mM |
| N-Methylisothiazolon-HCl | 0.01% |
| Oxy-Pyrion | 0.1% |
| Polydocanol | 0.25% | pH 7.2

The buffer used for the detection antigen comprises the following components:

| Buffer component | conc |
|---|---|
| MES | 50 mM |
| NaCl | 150 mM |
| N-Methylisothiazolon-HCl | 0.01% |
| Oxy-Pyrion | 0.1% |
| Polydocanol | 0.25% | pH 5.4

Example 3

Detection of Anti-p53 Auto-Antibodies in Clinical Samples

Samples from 463 patients were analyzed side by side for anti-p53 antibodies using the anti-p53 assay as described in Example 2 and the commercially available assay "MESACUP Anti-p53 TEST" distributed by MEDICAL & BIOLOGICAL LABORATORIES CO., LTD., KDX Nagoya, Japan. The later was used according to the instructions given by the manufacturer.

| | Number of samples | Elecsys | Mesacup |
|---|---|---|---|
| | | Sensitivity | Sensitivity |
| Colorectal cancer (CRC) | 88 | 32.95% | 39.77% |
| | | Spezifität | Spezifität |
| Controls from CRC screening | 43 | 97.60% | 86.05% |
| IBD (infectious bowel diseases) | 128 | 96.90% | 79.69% |
| osteoarthritis | 35 | 100% | 80.00% |
| Rheumatoid arthritis | 27 | 96.30% | 81.48% |
| Liver cirrhosis | 17 | 100% | 70.59% |
| Renal failure | 18 | 100% | 83.33% |
| Autoimmun diseases | 40 | 100% | 90.00% |

As can be seen from the above table, the newly anti-p53 antibody assay detects a comparable amount or slightly less of anti-p53 positive samples in colorectal cancer patients as compared to the competitor assay.

Strikingly the newly developed assay, however, is by far less prone to "positive" signals in disease entities not known to be associated with antibodies to p53.

Figure 2:
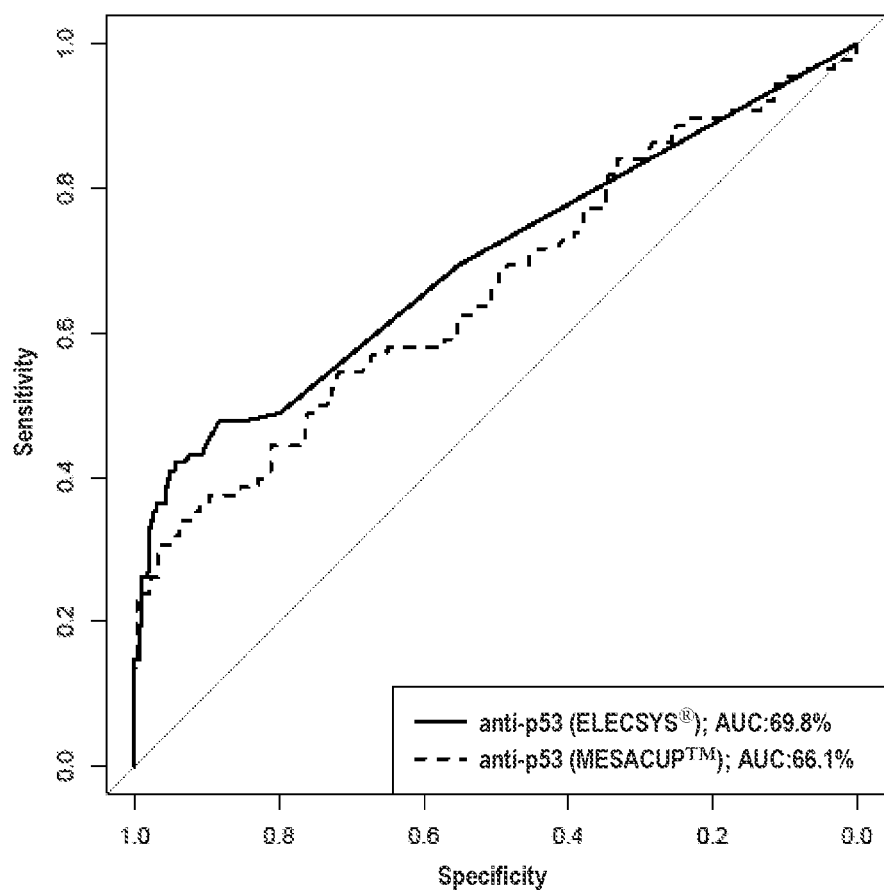

As shown in FIG. 2, the area under the curve (AUC) is better for the assays developed here as compared to a commercially available kit.

Most likely the positive measurements found in patients with, controls from CRC screening, IBD (infectious bowel diseases), osteoarthritis, rheumatoid arthritis, liver cirrhosis, renal failure or autoimmun diseases represent false positive measurements. Only very few false positive samples are seen with the new assay, whereas the state of the art assay very often would lead to a false positive results. Obviously, some of the additional positives found with the competitor assay in the CRC cases shown above quite likely are false positives for anti-p53 competitor assay.

The newly developed assay for the in vitro detection of anti-p53 antibodies as disclosed herein has a very good specificity. Such good specificity e.g. translates into less clinical work-up with patients erroneously found as anti-p53 antibody positive.

The invention claimed is:

1. An in vitro method for detecting an anti-tumor protein p53 (anti-p53) antibody in a sample having or suspected of having the anti-p53 antibody, the method comprising:
   a) incubating the sample with a p53 capture antigen and a p53 detection antigen, the p53 detection antigen comprising the peptide of SEQ ID NO:1 at least twice, whereby a complex comprising the p53 capture antigen, the anti-p53 antibody, and the p53 detection antigen is formed,
   b) separating the complex formed in (a) from unbound p53 detection antigen, and
   c) measuring the complex separated in step (b) via the p53 detection antigen comprised therein, thereby detecting the anti-p53 antibody.

2. The method according to claim 1, wherein the p53 capture antigen is capable of binding to a solid phase.

3. The method according to claim 2, wherein the p53 capture antigen is covalently bound to a first partner of a binding pair and wherein a second partner of said binding pair is bound to the solid phase.

4. The method according to claim 3, wherein the first partner of the binding pair is selected from the group consisting of hapten, biotin, a biotin analogue, DsF and a ligand for a receptor and wherein the second partner of said binding pair is selected from the group consisting of anti-hapten antibody, avidin, streptavidin, FimG DsF, and a ligand-receptor.

5. The method according to claim 2, wherein the p53 capture antigen is biotinylated and wherein the solid phase is coated with avidin or streptavidin.

6. The method according to claim 2, wherein the p53 capture antigen is bound to the solid phase.

7. The method according to claim 1, wherein the p53 detection antigen comprises a directly detectable label.

8. The method according to claim 7, wherein the directly detectable label is selected from the group consisting of a luminescent label, a fluorescent label, a chemiluminescent label and an electrochemiluminescent label.

9. The method according to claim 8, wherein the directly detectable label is selected from the group consisting of a chemiluminescent and an electrochemiluminescent label.

10. The method according to claim 1, wherein the p53 capture antigen comprises a peptide of SEQ ID NO: 1.

11. The method according to claim 1, wherein both the p53 capture antigen and the p53 detection antigen comprise a peptide of SEQ ID NO: 2.

12. The method according to claim 1, wherein the p53 detection antigen comprises both the peptides of SEQ ID NO:1 and of SEQ ID NO:2 at least twice.

13. The method according to claim 1, wherein the p53 detection antigen further comprises at least one multimerization domain and at least one polypeptide of SEQ ID NO:2, wherein the multimerization domain is a prokaryotic or eukaryotic chaperone selected from the group consisting of FKBP-type peptidyl-prolyl cis-trans isomerase (FkpA), Seventeen Kilodalton Protein (Skp), protein export chaperone SecB (SecB), heat shock protein 25 (Hsp25), macrophage infectivity potentiator (MIP), heat shock protein 60 (Hsp60/GroEL), caseinolytic mitochondrial matrix peptidase chaperone subunit B (ClpB) and caseinolytic mitochondrial matrix peptidase chaperone subunit X (ClpX).

14. The method according to claim 1, wherein the p53 detection antigen comprises an indirectly detectable label.

15. The method of claim 4, wherein the hapten is selected from the group consisting of biotin, a biotin analogue, sterols, a bile acid, a sexual hormone, a corticoid, a cardenolide, a cardenolide-glycoside, a bufadienolide, a steroid-sapogenine, a steroid alkaloid, and fluorescein.

16. The method of claim 15, wherein the biotin analogue is selected from the group consisting of aminobiotin, iminobiotin or desthiobiotin.

17. The method according to claim 1, wherein the p53 detection antigen further comprises at least one multimerization domain, wherein the multimerization domain is a prokaryotic or eukaryotic chaperone selected from the group consisting of FKBP-type peptidyl-prolyl cis-trans isomerase (FkpA), Seventeen Kilodalton Protein (Skp), protein export chaperone SecB (SecB), heat shock protein 25 (Hsp25), macrophage infectivity potentiator (MIP), heat shock protein 60 (Hsp60/GroEL), caseinolytic mitochondrial matrix peptidase chaperone subunit B (ClpB) and caseinolytic mitochondrial matrix peptidase chaperone subunit X (ClpX).

18. The method according to claim 13, wherein the p53 detection antigen comprises both the peptides of SEQ ID NO:1 and of SEQ ID NO:2 at least twice.

* * * * *

SEQUENCE LISTING

<160> NUMBER OF SEQ ID NOS: 4

<210> SEQ ID NO 1
<211> LENGTH: 25
<212> TYPE: PRT
<213> ORGANISM: Homo sapiens

<400> SEQUENCE: 1

Glu Pro Pro Leu Ser Gln Glu Thr Phe Ser Asp Leu Trp Lys Leu Leu
1               5                   10                  15

Pro Glu Asn Asn Val Leu Ser Pro Leu
            20                  25

<210> SEQ ID NO 2
<211> LENGTH: 20
<212> TYPE: PRT
<213> ORGANISM: Homo sapiens

<400> SEQUENCE: 2

Asp Asp Leu Met Leu Ser Pro Asp Asp Ile Glu Gln Trp Phe Thr Glu
1               5                   10                  15

Asp Pro Gly Pro
            20

<210> SEQ ID NO 3
<211> LENGTH: 393
<212> TYPE: PRT
<213> ORGANISM: Homo sapiens

<400> SEQUENCE: 3

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
            85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
            165                 170                 175

Pro His His Glu Arg Cys Ser Asp Ser Asp Gly Leu Ala Pro Pro Gln
        180                 185                 190

His Leu Ile Arg Val Glu Gly Asn Leu Arg Val Glu Tyr Leu Asp Asp
    195                 200                 205

Arg Asn Thr Phe Arg His Ser Val Val Val Pro Tyr Glu Pro Pro Glu
    210                 215                 220

```
Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
            245                 250                 255

Leu Glu Asp Ser Ser Gly Asn Leu Leu Gly Arg Asn Ser Phe Glu Val
        260                 265                 270

Arg Val Cys Ala Cys Pro Gly Arg Asp Arg Arg Thr Glu Glu Glu Asn
    275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
        370                 375                 380

Phe Lys Thr Glu Gly Pro Asp Ser Asp
385                 390

<210> SEQ ID NO 4
<211> LENGTH: 293
<212> TYPE: PRT
<213> ORGANISM: Artificial sequence
<220> FEATURE:
<223> OTHER INFORMATION: Homo sapiens

<400> SEQUENCE: 4

Met Ala Asp Lys Ile Ala Ile Val Asn Met Gly Ser Leu Phe Gln Gln
1               5                   10                  15

Val Ala Gln Lys Thr Gly Val Ser Asn Thr Leu Glu Asn Glu Phe Arg
            20                  25                  30

Gly Arg Ala Ser Glu Leu Gln Arg Met Glu Thr Asp Leu Gln Ala Lys
        35                  40                  45

Met Lys Lys Leu Gln Ser Met Lys Ala Gly Ser Asp Arg Thr Lys Leu
    50                  55                  60

Glu Lys Asp Val Met Ala Gln Arg Gln Thr Phe Ala Gln Lys Ala Gln
65                  70                  75                  80

Ala Phe Glu Gln Asp Arg Ala Arg Arg Ser Asn Glu Glu Arg Gly Lys
            85                  90                  95

Leu Val Thr Arg Ile Gln Thr Ala Val Lys Ser Val Ala Asn Ser Gln
        100                 105                 110

Asp Ile Asp Leu Val Val Asp Ala Asn Ala Val Ala Tyr Asn Ser Ser
    115                 120                 125

Asp Val Lys Asp Ile Thr Ala Asp Val Leu Lys Gln Val Lys Gly Gly
130                 135                 140

Gly Ser Gly Gly Gly Ser Gly Gly Gly Ser Gly Gly Gly Ser Gly Gly
145                 150                 155                 160

Gly Ser Glu Pro Pro Leu Ser Gln Glu Thr Phe Ser Asp Leu Trp Lys
            165                 170                 175

Leu Leu Pro Glu Asn Asn Val Leu Ser Pro Leu Pro Ser Gln Ala Met
        180                 185                 190
```

-continued

```
Asp Asp Leu Met Leu Ser Pro Asp Asp Ile Glu Gln Trp Phe Thr Glu
        195                 200                 205

Asp Pro Gly Pro Gly Gly Gly Ser Gly Gly Gly Ser Gly Gly Gly Ser
        210                 215                 220

Gly Gly Gly Ser Gly Gly Gly Ser Glu Pro Pro Leu Ser Gln Glu Thr
225                 230                 235                 240

Phe Ser Asp Leu Trp Lys Leu Leu Pro Glu Asn Asn Val Leu Ser Pro
                245                 250                 255

Leu Pro Ser Gln Ala Met Asp Asp Leu Met Leu Ser Pro Asp Asp Ile
            260                 265                 270

Glu Gln Trp Phe Thr Glu Asp Pro Gly Pro Gly Gly Ser His His His
        275                 280                 285

His His His His His
    290
```